(12) United States Patent
Ishii et al.

(10) Patent No.: US 7,750,162 B2
(45) Date of Patent: Jul. 6, 2010

(54) PROCESS FOR PREPARATION OF NONNATURAL AMINO ACID AND INTERMEDIATE THEREOF

(75) Inventors: Yutaka Ishii, Osaka (JP); Ryosuke Fujimoto, Osaka (JP)

(73) Assignee: Daiso Co., Ltd., Osaka (JP)

( * ) Notice: Subject to any disclaimer, the term of this patent is extended or adjusted under 35 U.S.C. 154(b) by 894 days.

(21) Appl. No.: 11/578,788

(22) PCT Filed: Apr. 18, 2005

(86) PCT No.: PCT/JP2005/007387

§ 371 (c)(1),
(2), (4) Date: Oct. 18, 2006

(87) PCT Pub. No.: WO2005/102991

PCT Pub. Date: Nov. 3, 2005

(65) Prior Publication Data

US 2007/0208180 A1    Sep. 6, 2007

(30) Foreign Application Priority Data

Apr. 19, 2004    (JP) .............................. 2004-122808

(51) Int. Cl.
C07D 213/00 (2006.01)
C07D 213/55 (2006.01)
C07C 269/00 (2006.01)
C07C 271/00 (2006.01)
(52) U.S. Cl. .................... 546/309; 546/335; 560/24
(58) Field of Classification Search ...................... None
See application file for complete search history.

(56) References Cited

U.S. PATENT DOCUMENTS 6,410,576 B1    6/2002  Nishimura et al.
2003/0207920 A1  11/2003  Altenburger et al.

FOREIGN PATENT DOCUMENTS

JP    8-231516    9/1996
JP    2003-528098  9/2003

OTHER PUBLICATIONS

Danishefsky et al, Tetrahedron Letters, An Approach to the Synthesis of the Naphthyrinomycin Alkaloids: The Synthesis of Two Subunits, 25 (38), pp. 4199-4202).*
Alekseeva et al, Zhurnal Organicheskoi Khimii, Synthesis and Study of Compounds With Potential Biological Activity. V. Dialkylamino-Derivatives of Glutamic Acid, 1971, 7(4), pp. 645-647, Abstract.*
A. Marini et al., "Utilisation des organocuprates dans la synthese des α-aminoacides heterocycliques", Bull. Soc. Chim. Fr., pp. 554-558, 1989 (Abstract in English).
R. F. W. Jackson et al., "Preparation of Enantiomerically Pure Protected 4-Oxo-α-amino Acids and 3-Aryl-α- amino Acids from Serine", J. Org. Chem., vol. 57, pp. 3397-3404, 1992.

(Continued)

Primary Examiner—Paul A Zucker
(74) Attorney, Agent, or Firm—Wenderoth, Lind & Ponack, L.L.P.

(57) ABSTRACT

A process for the preparation of a nonnatural amino acid represented by the following formula (C):

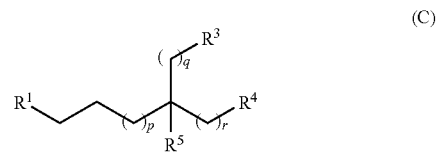

(C)

which is characterized by reacting a compound represented by the following formula (A1), a compound represented by the following formula (A2) and a compound represented by the following formula (A3) (step 1):

$$R^1—X^1,$$ (A1)

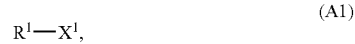

(A2)

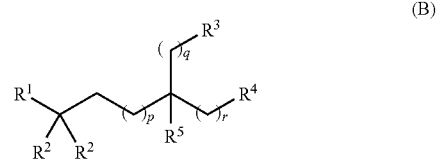

(A3)

to form a compound represented by the following formula (B):

(B)

and then subjecting the compound (B) to deprotection of protective groups of carboxyl groups and to decarboxylation (wherein $X^1$ and $X^2$ are a leaving group, $R^1$ is an aromatic group, an unsaturated heterocyclic group, or $R^6CO$ group, $R^2$ and $R^3$ are a protected carboxyl group, $R^4$ is a protected amino group, $R^5$ is hydrogen atom, an aliphatic hydrocarbon group, an aromatic group, or a heterocyclic group, $R^6$ is an aromatic group or an unsaturated heterocyclic group, etc., and p, q and r are an integer of 0 to 10).

13 Claims, No Drawings

OTHER PUBLICATIONS

P. N. Collier et al., "The direct synthesis of novel enantiomerically pure α-amino-acids in protected form via Suzuki cross-coupling", Tetrahedron Letters, vol. 41, pp. 7115-7118, 2000.

N. T. Boggs et al., "Studies on the Synthesis and Resolution of γ-Carboxyglutamic Acid Derivatives", J. Org. Chem., vol. 44, No. 13, pp. 2262-2269, 1979.

E. N. Chauvel et al., "Differential Inhibition of Aminopeptidase A and Aminopeptidase N by New β-Amino Thiols", J. Med. Chem., vol. 37, pp. 2950-2957, 1994.

P. Ciapetti et al., "Nucleophilic Substitution of Protected 2-Amino-4-Butanoic Acid. An Easy Route to Exotic Amino Acids and Conformationally Constrained Peptides.", Tetrahedron Letters, vol. 39, pp. 3843-3846, 1998.

M. Amblard et al.,"Synthesis and Biological Evaluation of Cholecystokinin Analogs in Which the Asp-Phe-$NH_2$ Moiety has been Replaced by a 3-Amino-7-phenylheptanoic Acid or a 3-Amino-6-(phenyloxy)hexanoic Acid", J. Med. Chem., vol. 36, pp. 3021-3028, 1993.

N. Selvakumar et al., "Dimethyl Imalonate as a one-carbon source: a novel method of introducing carbon substituents onto aromatic nitro compounds", Tetrahedron Letters, vol. 42, pp. 8395-8398, 2001.

XP002471358 (Abstract: J. Heterocycl. Chem., vol. 28, No. 7, 1991, pp. 1757-1768).

J. M. Altenburger et al., "SSR182289A, A Selective and Potent Orally Active Thrombin Inhibitor", Bioorganic & Medicinal Chemistry, vol. 12, pp. 1713-1730, 2004.

XP002471359 (Abstract: J. Chem. Soc. Perkin Trans., 1, vol. 12, pp. 1903-1912, 1998.

* cited by examiner

PROCESS FOR PREPARATION OF NONNATURAL AMINO ACID AND INTERMEDIATE THEREOF

This application is a U.S. national stage of International Application No. PCT/JP2005/007387 filed Apr. 18, 2005.

TECHNICAL FIELD

The present invention relates to a process for the preparation of a nonnatural amino acid, a process for the preparation of its intermediate and the intermediate.

BACKGROUND ART

In these years, application of a nonnatural amino acid and a compound including a nonnatural amino acid to medicaments or agrochemicals has been progressed. It has been in a large numbers reported that especially, a nonnatural amino acid which has an aromatic group or a heterocyclic group in a terminal side chain thereof exhibits biologically interested activities and application to new medicaments or agrochemicals has been expected. Some processes of the preparation of nonnatural amino acids which have an aromatic group or a heterocyclic group in a terminal side chain thereof have been reported. However, as a process for the preparation utilizing C—C bond-formation reaction (coupling reaction) at a side chain in the amino acid, there are known the processes utilizing an organic metal regent such as cupper or palladium (See, for example nonpatent documents 1~3.). However, there are following troubles: the organic metal reagent is generally expensive, the handling is troublesome, and purification procedure of the amino acid is difficult. Therefore, the development of an industrially effective process for the preparation thereof has been desired.

On the other hand, a process for the preparation of a nonnatural amino acid by coupling diethyl malonate to a side chain of an amino acid is reported (See, for example nonpatent documents 4~6.). However, the examples of utility of a nonnatural amino acid which has malonic acid as a side chain, which have been reported are within the scope considered from malonic acid synthesis, namely remain only in elimination of one carbon dioxide molecule from malonic acid moiety. The method therefore, could not be applied to a process for the preparation of a nonnatural amino acid which has an aromatic group or a heterocyclic group in a terminal side chain thereof which needs elimination of two carbon dioxide molecules from the malonic acid moiety.

Nonpatent document 1: El Marini, A. et al., Bull. Soc. Chim. Fr., 554-558 (1989)

Nonpatent document 2: Jackson, R. F. W. et al., J. Org. Chem., 57, 3397-3404 (1992)

Nonpatent document 3: Collier, F. N. et al., Tetrahedron Lett., 41, 7115-7119 (2000)

Nonpatent document 4: Boggs, N. T. et al., J. Org. Chem., 44, 2262-2269 (1979)

Nonpatent document 5: Chauvel, E. N. et al., J. Med. Chem., 37, 2950-2957 (1994)

Nonpatent document 6: Ciapetti, P. et al., Tetrahedron Lett., 39, 3843-3846(1998)

DISCLOSURE OF INVENTION

The problem is to provide an effective process for the preparation of a nonnatural amino acid, and its intermediate useful for the process.

The present inventors have earnestly studied to address the above problem and have studied a novel process for the preparation of a nonnatural amino acid, and as a result, have found a novel process for the preparation of a nonnatural amino acid, its intermediate and a process for the preparation of its intermediate, by applying malonic acid as a key compound.

The present invention relates to a process for the preparation of a nonnatural amino acid represented by the following formula (C):

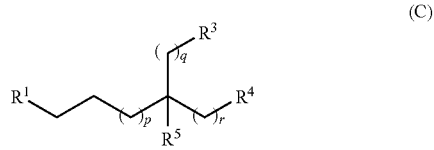

(C)

which is characterized by reacting a terminal constituent compound represented by the following formula (A1), a malonic acid derivative represented by the following formula (A2) and a starting material amino acid represented by the following formula (A3):

(A1)

(A2)

(A3)

to prepare a compound represented by the following formula (B) (step 1):

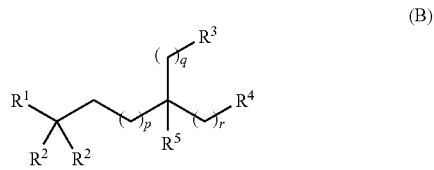

(B)

and then subjecting the compound (B) to deprotection of protective groups of carboxyl groups in $R^2$ and to decarboxylation to prepare said compound (C) (step 2)

wherein $X^1$ and $X^2$ are a leaving group, $R^1$ is a substituted or unsubstituted aromatic group, a substituted or unsubstituted and unsaturated heterocyclic group, or $R^6CO$ group, $R^2$ and $R^3$ are independently a protected carboxyl group, $R^4$ is a protected amino group, $R^5$ is hydrogen atom, a substituted or unsubstituted and saturated or unsaturated aliphatic hydrocarbon group, a substituted or unsubstituted aromatic group, or a substituted or unsubstituted and saturated or unsaturated heterocyclic group, $R^6$ is a substituted or unsubstituted and saturated or unsaturated aliphatic hydrocarbon group, a substituted or unsubstituted aromatic group, or a substituted or unsubstituted and saturated or unsaturated heterocyclic group, and p, q and r are independently an integer of 0 to 10.

The present invention, as shown in the following reaction scheme, is to prepare the intermediate (B) starting from a terminal constituent compound (A1), the malonic acid derivative (A2) and the starting material amino acid (A3), and then to subject the compound (B) to deprotection of protective groups of carboxyl groups in the malonic acid moiety of the intermediate (B) and to elimination of two carbon dioxide molecules to prepare the nonnatural amino acid (C).

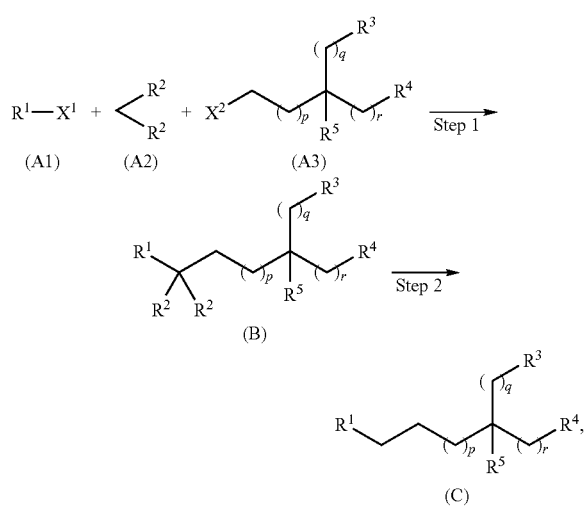

wherein each of signals is the same as defined above.

The present invention also relates to a process for the preparation of a nonnatural amino acid which is characterized by deprotecting protective groups of carboxyl groups in the malonic acid moiety of the intermediate (B) and then subjecting to elimination of two carbon dioxide molecules (decarboxylation) to give the above mentioned nonnatural amino acid (C) (step 2).

The present invention also relates to the novel compound which is used for the above reaction and represented by the following formula (B):

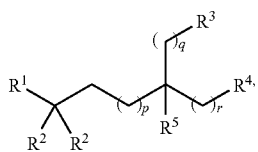

wherein $R^1$ is a substituted or unsubstituted aromatic group, a substituted or unsubstituted and unsaturated heterocyclic group, or $R^6CO$ group, $R^2$ and $R^3$ are independently a protected carboxyl group, $R^4$ is a protected amino group, $R^5$ is hydrogen atom, a substituted or unsubstituted and saturated or unsubstituted aliphatic hydrocarbon group, a substituted or unsubstituted aromatic group, or a substituted or unsubstituted and saturated or unsaturated heterocyclic group, $R^6$ is a substituted or unsubstituted and saturated or unsaturated aliphatic hydrocarbon group, a substituted or unsubstituted aromatic group, or a substituted or unsubstituted and saturated or unsaturated heterocyclic group, and p, q and r are independently an integer of 0 to 10.

The terminal constituent compound (A1), the malonic acid derivative (A2) and a starting material amino acid (A3), which are respectively an important constituent of the present invention are in detail explained below.

The terminal constituent compound (A1) used in the present invention, is an aromatic compound or an unsaturated heterocyclic compound having a leaving group $X^1$ for receiving a nucleophilic substitution reaction by the malonic acid derivative, or a compound formed by binding $R^6$ such as an aromatic group or an unsaturated heterocyclic group with $X^1$ via CO.

$R^1$ in the terminal constituent compound (A1) means a substituted or unsubstituted aromatic group, a substituted or unsubstituted and unsaturated heterocyclic group, or $R^6CO$ group.

The aromatic group in $R^1$ includes a 5 to 8 membered monocyclic aromatic group and a polycyclic aromatic group prepared by condensing these two or more aromatic rings, such as phenyl, naphthyl, phenanthyl, anthranyl, etc. The substituents on said aromatic group include a group or an atom which is generally known in the organic chemistry such as alkyl, alkenyl, alkynyl, aryl, halo, haloformyl, hydroxy, alkoxy, oxo, oxycarbonyl, carboxy, carbamoyl, phosphino, amino, imino, thio, mercapto, sulfo, sulfenyl, sulfonyl, cyano, nitro, nitroso, azo, diazo, azido, hydrazino, isocyanate, sillyl or an organic metal. Said substituents may be further substituted.

The unsaturated heterocyclic group in $R^1$ includes an aromatic or non aromatic group as far as the ring contains at least one hetero atom in the ring. The hetero atom in the unsaturated heterocyclic group is nitrogen, oxygen, sulfur, phosphorous, selenium, etc. Two or more hetero atoms may be contained in the ring. The unsaturated heterocyclic group may have a carbonyl group in the ring such as oxazolonyl group.

The unsaturated heterocyclic group includes an aromatic group, such as furyl, thienyl, imidazolyl, oxazolyl, thiazolyl, pyridyl, pyrimidinyl, pyridazinyl, pyrazinyl, triazolyl, quinolyl, etc.; a non aromatic group, such as oxazolidinyl, imidazolidinyl, thiazolidinyl, etc. The unsaturated heterocyclic ring containing nitrogen atom includes imidazolyl, oxazolyl, thiazolyl, pyridyl, pyrimidinyl, pyridazinyl, pyrazinyl, triazolyl, quinolyl, oxazolidinyl, imidazolidinyl, thiazolidinyl, etc. The substituents on the unsaturated heterocyclic group include the same substituents as shown as the substituents on the above aromatic group.

$R^6$ in $R^6CO$ group of $R^1$ means the same group as mentioned in $R^5$ below except hydrogen atom, preferably a substituted or unsubstituted aromatic group and a substituted or unsubstituted and unsaturated heterocyclic group.

$X^1$ in the terminal constituent compound (A1) means a leaving group. The leaving group on the aromatic compound or unsaturated heterocyclic compound having $X^1$ includes halo such as fluoro, chloro, bromo, or iodo; sulfonyloxy such as methanesulfonyl(mesyl)oxy, toluenesulfonyl(tosyl)oxy, nitrobenzenesulfonyl(nosyl)oxy, trifluoromethanesulfonyloxy; alkoxy; alkyloxycarbonyloxy; hydroxy; carboxy, etc., preferably halo such as fluoro, chloro, bromo, or iodo and sulfonyloxy such as methanesulfonyl(mesyl)oxy, toluenesulfonyl(tosyl)oxy, nitrobenzenesulfonyl(nosyl)oxy, trifluoromethanesulfonyloxy.

The leaving group bound to $R^6CO$ includes halo such as fluoro, chloro, bromo, iodo; alkoxy; alkyloxycarbonyloxy; hydroxy; carboxy, etc., preferably halo such as fluoro, chloro, bromo, or iodo.

The malonic acid derivative (A2) used in the present invention includes malonic acid diester and Meldrum's acid (isopropylidene malonate).

$R^2$ in the malonic acid derivative (A2) means a protected carboxyl group. The protected carboxyl group includes methoxycarbonyl group, ethoxycarbonyl group, propoxycarbonyl group, isopropoxycarbonyl group, butoxycarbonyl group, allyloxycarbonyl group, benzyloxycarbonyl group, 4-nitrobenzyloxycarbonyl group, or tert-butoxycarbonyl group. Further Meldrum's acid which is prepared by ring closure of two carboxyl groups can be used as an equivalent compound to malonic acid in the present invention.

The starting material amino acid (A3) used in the present invention is an amino acid having $X^2$, a leaving group which receives nucleophilic substitution reaction by the malonic acid derivative (A2).

$X^2$ in the starting material amino acid (A3) means the same leaving group as mentioned in the above $X^1$, and $R^3$ means the same protected carbonyl group as $R^2$. The leaving group, $X^2$ is preferably, iodo, bromo, mesyloxy, tosyloxy, trifluoromethanesulfonyloxy or nosyloxy.

$R^4$ in the starting material amino acid (A3) means a protected amino group. The protected amino group includes acylamino, alkyloxycarbonylamino, sulfonylamino, N-phthalimide, etc., preferably alkyloxycarbonylamino group. The compound which $R^3$ and $R^4$ in the starting material amino acid (A3) are together protected to form, such as oxazolone or hydantoin may be used as an equivalent compound to the starting material amino acid (A3).

$R^5$ in the starting material amino acid (A3) means hydrogen atom, a substituted or unsubstituted and saturated or unsaturated aliphatic hydrocarbon group, a substituted or unsubstituted aromatic group, or a substituted or unsubstituted and saturated or unsaturated heterocyclic group. The saturated or unsaturated aliphatic hydrocarbon group includes a saturated aliphatic hydrocarbon group, namely alkyl group such as methyl, ethyl, propyl, isopropyl, butyl, isobutyl, t-butyl, pentyl, etc., an aliphatic hydrocarbon group having an unsaturated bond such as a double bond between C—C or a triple bond between C—C, namely an alkenyl group such as vinyl, allyl, isopropenyl, butenyl, isobutenyl, pentenyl, etc., an alkynyl group such as ethynyl, propynyl, butynyl, pentynyl, etc., and these groups may be a straight or branched chain. The substituents on the aliphatic hydrocarbon group include the same substituents as the substituents on the above mentioned aromatic group. The aliphatic hydrocarbon group includes one substituted by an aromatic group, namely aralkyl, aralkenyl, or aralkynyl. The aralkyl group includes benzyl or phenethyl, etc. Carbon number of the aliphatic hydrocarbon is not limited, but preferably 1 to 30, more preferably 1 to 20. Number of the constitution member of the cyclic aliphatic hydrocarbon group is preferably 3 to 10, and more preferably 5 to 7.

The saturated heterocyclic group includes a so-called aliphatic heterocyclic compound (group) such as pyrrolidinyl, piperazinyl, tetrahydrofuryl, 1,3-dithianyl, lactone ring, lactum ring, etc. The substituents on the saturated heterocyclic group includes the same ones as the substituents on the above mentioned aromatic group.

The aromatic group and unsaturated heterocyclic ring (group) respectively mean the same as ones in the above mentioned $R^1$.

As the carbon atom substituted by $R^5$ is an asymmetric carbon atom, the starting material amino acid (A3) may be used either in optically active form or racemate. The amino acid (A3) having other asymmetric carbon except said carbon atom may be used.

In the starting material amino acid (A3), p, q and r are independently an integer of 0 to 10. Various amino acids such as α-amino acid (q=r=0), β-amino acid (q+r=1), γ-amino acid (q+r=2), etc., may be used in the present invention. The number of p, q and r is not limited, but preferably 0 to 5, more preferably 0 to 3.

The step 1 in the present invention is in detail explained below.

The intermediate (B) in the step 1 is prepared by reacting in a suitable solvent in the presence of a suitable base under the usual condition which is known in alkylation/arylation reaction of a malonic acid derivative (See, for example, J. Mathieu, J. Weill-Raynal, Formation of C—C Bonds, vol. 2, Germany (Georg Thieme Publishers), 1975, p. 2-279, p. 371-386).

The base includes one which is described in the above literature such as lithium, sodium, potassium, sodium amide, potassium tert-butoxide, sodium hydride, lithium diisopropylamide, sodium hydroxide, potassium carbonate, sodium carbonate, sodium hydrogencarbonate, potassium hydrogencarbonate, sodium acetate, etc. Sodium hydride, potassium tert-butoxide, and potassium carbonate are preferable in point of yield. Potassium carbonate is more preferably because of prevention of racemization on the amino acid part. These bases can be used in combination of them.

The solvents include an ether-solvent (e.g., diethyl ether, diisopropylpropyl ether, dibutyl ether, 1,2-dimethoxyethane, diglyme, tert-butyl methyl ether, tetrahydrofuran (THF), dioxane, cyclopropyl methyl ether, etc.), an alcohol-solvent (e.g., methanol, ethanol, isopropanol, tert-butanol, etc.), an aromatic solvent (e.g., benzene, toluene, xylene, ethylbenzene, styrene, anisole, N,N-dimethylaniline (DMF), chlorobenzene, methyl benzoate, etc.), an ester-solvent (e.g., ethyl acetate, etc.), a ketone-solvent (e.g., acetone, methyl ethyl ketone, methyl isobutyl ketone, etc.) and an aprotic solvent (e.g., acetonitrile, N,N-dimethylformamide, dimethyl sulfoxide, etc.), and water. Especially a ketone-solvent, an aprotic solvent, and an ether-solvent are preferable in point of yield. The ketone-solvent is more preferable in points of cost and handling. These solvents can be used in combination of them. A heterogeneous solvent together with phase-transfer catalyst can be also used.

The reaction is carried out usually at −20° C. to 130° C.

In the process for the preparation of the intermediate (B), the reaction order of the terminal constituent (A1), the malonic acid derivative (A2) and the starting material amino acid (A3) is not limited. Namely, after reaction of the terminal constituent (A1) and the malonic acid derivative (A2), the starting material amino acid (A3) can be reacted therewith to prepare the intermediate (B) (method a), or after reacting the starting material amino acid (A3) and the malonic acid derivative (A2), the terminal constituent compound (A1) can be reacted therewith to prepare the intermediate (B) (method b). Furthermore, three compounds of the terminal constituent compound (A1), the malonic acid derivative (A2) and the starting amino acid (A3) may be together reacted in one system, so-called by one pot method to prepare the intermediate (B) (method c). Especially, the above "method a" is best in point of yield.

When the leaving group $X^2$ in the starting material amino acid (A3) is except iodo, the reaction can be promoted by adding iodide ion such as NaI as catalyst.

The step 2 in the present invention is in detail explained below.

The step 2 relates to a process for the preparation of the nonnatural amino acid (C) which comprises deprotecting protective groups of carboxyl groups ($R^2$) in the malonic acid moiety of the said intermediate (B) and subjecting to elimination of two carbon dioxide molecules to give the nonnatural amino acid (C).

Protective groups of carboxyl groups in $R^2$ of the intermediate (B) in the step 2 are deprotected by using a generally known deprotection method on the compound containing an amino acid as a constituent. For example, acid hydrolysis, base hydrolysis and hydrogenolysis are illustrated.

In case of acid hydrolysis, preferable $R^2$ is tert-butoxycarbonyl group, and said group for example, is treated with trifluoroacetic acid in the absent or present of the solvent such as dichloromethane, chloroform, and then neutralized to be deprotected.

The reaction is carried out usually at −10 to 50° C.

In case of base hydrolysis, preferable $R^2$ is an ester formed with a lower alkyl group, such as methoxycarbonyl group, or ethoxycarbonyl group. For example, said group is usually treated with a base such as sodium hydrogencarbonate, sodium carbonate, potassium carbonate, sodium hydroxide, potassium hydroxide, lithium hydroxide, etc., in the presence of a mixture of water and a solvent such as methanol, ethanol, THF or dioxane, and then neutralized to be deprotected.

The reaction is carried out usually at −10 to 80° C.

In case of hydrogenolysis, preferable $R^2$ is benzyloxycarbonyl group, 4-nitrobenzyloxycarbonyl group, 4-chlorobenzyloxycarbonyl group, etc. For example, the hydrogenolysis is carried out by reacting with hydrogen in the presence of catalyst such as Raney nickel, or palladium-carbon catalyst, or by reacting in the presence of palladium-carbon catalyst with hydrogen-donor such as ammonium formate, or cyclohexene.

The solvent used in this reaction includes water, methanol, ethanol, acetic acid, dioxane, THF, etc. This reaction is carried out usually at 0 to 100° C. under ordinary or higher pressure.

After deprotection of the protective group of the carboxyl group in $R^2$ of the intermediate (B) in the step 2, the process for preparing a nonnatural amino acid (C) by elimination of two carbon dioxide molecules is carried out by heating it in the absence or presence of a suitable solvent. The solvent is not specially limited, but preferably methanol, ethanol, propanol, acetone, ethyl acetate, toluene, xylene, mesitylene, DMF, DMSO, water, etc. These solvents may be used in combination of them.

The reaction is carried out usually at 10 to 140° C.

The elimination of two carbon dioxide molecules can be carried out under either acidic or basic condition, but is characterized in being carried out under neutral conditions. By conducting the reaction under neutral condition, elimination of the protecting group presenting in a nonnatural amino acid (C), and racemization on an asymmetric carbon of the amino acid part is controlled or prohibited, and therefore, it is beneficial for the preparation of the nonnatural amino acid (C). Herein the neutral condition means that the protected group of carboxyl group or amino group presenting on a nonnatural amino acid (C) is hardly eliminated or deprotected. As rough standard, after sufficiently or fully stirring the solution prepared by adding water (0.5 mL) to a solution of decarboxylation reaction (1 mL), pH of the phase containing much more water is in the range of 3 to 10.

In case of the elimination of two carbon dioxide molecules in the step 2, preferable $R^1$ in a nonnatural amino acid (C) is an electron-withdrawing substituent group. The decarboxylation from the malonic acid derivative usually stops with elimination of only one carbon dioxide molecule, but when $R^1$ is an electron-withdrawing substituent group, the elimination of the second carbon dioxide molecule is accelerated. The electron-withdrawing substituent group in $R^1$ includes an aromatic group and $R^6CO$ group (wherein $R^6$ is the same as defined above.) as a representative. The electron-withdrawing substituent includes not only an unsaturated heterocyclic group having aromaticity but also an unsaturated heterocyclic group (such as 2-oxazolidinyl group), which is formed by binding with a single bond between its unsaturated part and a central carbon atom of the malonic acid part derived from the formula (A2), although it is non aromatic. An unsaturated heterocyclic group containing nitrogen is especially preferable because it is high in electron-withdrawing. The aromatic group or unsaturated heterocyclic group which is substituted by electron-withdrawing substituent group, such as nitro group, cyano group, oxo group, alkoxycarbonyl group, trihalomethyl group, or carbamoyl group are further more preferable.

In the step 2, when the intermediate (B), wherein $R^1$, $R^5$ or $R^6$ is a group substituted by nitro group, is used and subjected to hydrogenolysis in order to deprotect a protective group of carboxyl group, a nonnatural amino acid (C) in which the nitro group is converted to amino group, is obtained. Furthermore, when the protective groups of $R^3$ and $R^4$ on the intermediate (B), which are hardly degraded in the condition of deprotection of $R^2$ are used, a nonnatural amino acid (C) remaining the protected carboxyl group ($R^3$) and the protected amino group ($R^4$) in the amino acid part can be prepared.

EFFECT OF INVENTION

According to the present invention, a nonnatural amino acid can be easily prepared with the method unknown before.

BEST MODE FOR CARRYING OUT THE INVENTION

The present invention is explained by examples below, but is not limited by these examples.

Reaction vessels: Vessels were dried by frame under a nitrogen atmosphere, and therein were poured substrates, nucleophilic reagents, catalysts, solvents, and so on.

Solvent: The solvents which were purified by distillation just before use were respectively used.

Analytical machine: $^1$H NMR was measured by GSX270 FT-NMR (JEOL datum LTD).

pH Measurement: After sufficiently or fully stirring the solution prepared by adding water (0.5 mL) to a solution of decarboxylation reaction (1 mL), pH of the phase containing much more water was measured with pH test paper.

Synthesis of Starting Materials:

(S)-Homoserine, N-(tert-butoxycarbonyl)-L-glutamic acid 1-benzyl ester, (S)-2-tert-butoxycarbonylamino-3-hydroxypropanoic acid methyl ester, dibenzyl malonate, diethyl malonate, diethyl phenylmalonate, and 2-chloro-5-nitropyridine were purchased from Tokyo Chemical Industry Co., Ltd.).

(S)-3-tert-Butoxycarbonylamino-4-benzyloxybutanoic acid was purchased from Fluka Chemie AG (Switzerland).

(S)-2-tert-Butoxycarbonylamino-4-methaesulfonyloxybutanoic acid methyl ester (1), (S)-2-benzyloxycarbonylamino-4-methanesulfonyloxybutanoic acid methyl ester (2), (S)-2-tert-butoxycarbonylamino-4-methanesulfonyloxybutanoic acid benzyl ester (3), and (S)-2-tert-butoxycarbonylamino-4-iodobutanoic acid methyl ester (4) were prepared starting from (S)-homoserine in accordance of the method described in the literature (Ohwada, J. et al., Chem. Pharm. Bull., 42, 1703-1705 (1994)).

(S)-2-tert-Butoxycarbonylamino-5-iodopentanoic acid benzyl ester (5) was prepared starting from N-(tert-butoxycarbonyl)-L-glutamic acid 1-benzyl ester in accordance of the method described in the literature (Jackson, R. F. W. et al., J. Org. Chem., 63, 7875-7884 (1998)).

(S)-2-tert-Butoxycarbonylamino-3-methanesulfonyloxypropaoic acid methyl ester (6) was starting from (S)-2-tert-butoxycarbonylamino-3-hydroxypropanoic acid methyl ester in accordance of the method described in the literature (Chauvel, E. N. et al., J. Med. Chem., 37, 2950-2957 (1994)).

(S)-3-tert-Butoxycarbonylamino-4-methanesulfonyloxybutanoic acid methyl ester (7) was prepared by methyl esterification, debenzylation and mesylation of (S)-3-tert-butoxycarbonylamino-4-benzyloxybutanoic acid.

Optical purity of optically active amino acid derivatives was 99% ee or more than 99% ee.

REFERENCE EXAMPLE 1

Dibenzyl 5-nitro-2-pyridylmalonate (8)

A solution of dibenzyl malonate (2.84 g, 10 mmol) in THF (10 ml) was gradually dropped to sodium hydride (800 mg, 20 mmol: 60%) in THF (20 ml) under a nitrogen atmosphere at room temperature. After cessation of evolution of hydrogen, thereto was gradually added 2-chloro-5-nitropyridine (1.59 g, 10 mmol) in THF (10 ml). The mixture was stirred for 24 hours at room temperature, and then neutralized with 1N hydrochloric acid. The resulted precipitate was dissolved by adding ethyl acetate (200 ml) thereto. The aqueous layer was separated and the organic layer was washed with saturated brine (30 mL), followed by concentration in vacuo. The residue was washed with hexane (50 mL×2) and dried to give the object compound (8) as an orange solid (3.29 g, yield 81%).

REFERENCE EXAMPLE 2

Diethyl 5-nitro-2-pyridylmalonate (9)

Diethyl malonate (1.60 g, 10 mmol) in THF (10 ml) was gradually dropped to sodium hydride (800 mg, 20 mmol: 60%) in THF (20 ml) under a nitrogen atmosphere at room temperature. After cessation of evolution of hydrogen, thereto was gradually added 2-chloro-5-nitropyridine (1.59 g, 10 mmol) in THF (10 ml). The mixture was stirred for 24 hours at room temperature, and then neutralized with 1N hydrochloric acid. The resulted precipitate was dissolved by adding ethyl acetate (200 ml) thereto. After separating the aqueous layer, the organic layer was washed with saturated brine (30 mL), and concentrated in vacuo. The residue was washed with hexane (50 mL×2) and dried to give the object compound (8) as a yellow solid (2.45 g, yield 87%).

REFERENCE EXAMPLE 3

1-Methyl, 6-benzyl (S)-2-tert-butoxycarbonylamino-5-benzyloxycarbonylhexanedicarboxylate (10)

Dibenzyl malonate (2.84 g, 10 mmol) in DMF (10 ml) was gradually dropped to sodium hydride (400 mg, 10 mmol: 60%) in DMF (20 ml) under a nitrogen atmosphere at room temperature. After cessation of evolution of hydrogen, thereto was gradually added the compound (4) (1.72 g, 5 mmol) in DMF (10 ml). The mixture was stirred for 20 hours at 70° C., neutralized under ice cooling with 1N hydrochloric acid, and the solvent was removed in vacuo. The residue was purified by column chromatography (hexane:ethyl acetate=5:1), and the solvent was removed in vacuo to give the object compound (10) as a pale yellow viscous liquid (1.35 g, yield 54%).

REFERENCE EXAMPLE 4

1-Methyl, 5-ethyl (S)-2-tert-butoxycarbonylamino-4-ethoxycarbonylpentane dicarboxylate (11)

Diethyl malonate (1.60 g, 10 mmol) in DMF (10 ml) was gradually dropped to sodium hydride (400 mg, 10 mmol: 60%) in DMF (20 ml) under a nitrogen atmosphere at 0° C. After cessation of evolution of hydrogen, thereto was gradually added the compound (6) (1.49 g, 5 mmol) in DMF (10 ml). The mixture was stirred for 20 hours at room temperature, the mixture was neutralized under ice cooling with 1N hydrochloric acid, and the solvent was removed in vacuo. The residue was purified by column chromatography (hexane: ethyl acetate=5:1), and the solvent was removed in vacuo to give the object compound (11) as a pale yellow viscous liquid (0.79 g, yield 44%).

EXAMPLE 1

6-Benzyl, 1-methyl (S)-2-tert-Butoxycarbonylamino-5-benzyloxycarbonyl-5-(5-nitropyridin-2-yl)-hexane dicarboxylate (12) (Method a)

After the compound (8) (4.06 g, 10 mmol) and the compound (4) (3.43 g, 10 mmol) were dissolved in acetone (100 mL) under a nitrogen atmosphere at room temperature, thereto was added potassium carbonate (6.9 g, 50 mmol), followed by refluxing at 55° C. for 24 hours. The solvent was removed in vacuo and the residue was dissolved by adding ethyl acetate (50 mL) and water (50 mL). After the aqueous layer was separated, the organic layer was washed with saturated brine (30 mL), concentrated in vacuo, and the residue was purified by column chromatography (hexane: ethyl acetate=3:1). The solvent was removed in vacuo to give the object compound (12) as a pale yellow viscous liquid (4.35 g, yield 70%).

$^1$H NMR (CDCl$_3$) δ: 1.40 (s, 9H), 1.50-1.80 (m, 2H), 2.49 (t, J=8.4Hz, 2H), 3.66 (s, 3H), 4.15-4.25 (m, 1H), 5.00-5.15 (br, 1H), 5.15 (s, 4H), 7.12-7.35 (m, 10H), 7.82 (d, J=8.6Hz, 1H), 8.39 (dd, J=8.6, 2.5Hz, 1H), 9.28 (d, J=2.5Hz, 1H).

EXAMPLE 2

Compound (12) (Method b)

Sodium hydride 60 mg (1.5 mmol: 60%) was added to THF (5 mL) under a nitrogen atmosphere at room temperature. Thereto was gradually added the compound (10) (499 mg, 1 mmol) in THF (2 mL). After cessation of evolution of hydrogen, thereto was gradually dropped 2-chloro-5-nitropyridine (159 mg, 1 mmol) in THF (2 mL). The mixture was stirred for 24 hours at 60° C., neutralized with 1N hydrochloric acid, and thereto was added ethyl acetate (5 mL). The water layer was separated and the organic layer was washed with saturated brine (10 mL), followed by removal of the solvent in vacuo. The residue was purified by column chromatography (hexane:ethyl acetate=3:1), and the solvent was removed in vacuo to give the object compound (12) (186 mg, yield 30%).

EXAMPLE 3

Compound (12) (Method c)

To acetone (10 mL) were added under a nitrogen atmosphere potassium carbonate (1.38 g, 10 mmol), 2-chloro-5-nitropyridine (317 mg, 2 mmol), dibenzyl malonate (568 mg, 2 mmol) and the compound (4) (686 mg, 2 mmol), and the mixture was stirred at 55° C. for 24 hours. After the removal of the solvent, the residue was dissolved by adding ethyl acetate (10 mL) and water (10 mL). The aqueous layer was removed, the organic layer was washed with saturated brine (10 mL) and concentrated in vacuo. The residue was purified by column chromatography (hexane:ethyl acetate=3:1) and the solvent was removed in vacuo to give the object compound (12) (311 mg, yield 25%).

EXAMPLE 4

1-Methyl, 6-ethyl (S) -2-benzyloxycarbonylamino-5-ethoxycarbony-5- (5-nitropyridin-2-yl)hexane dicarboxylate (13) (Method a)

After the compound (9) (2.82 g, 10 mmol) and the compound (2) (3.45 g, 10 mmol) were dissolved in acetone (100 mL) under a nitrogen atmosphere at room temperature, thereto were added potassium carbonate (6.9 g, 50 mmol) and sodium iodide (0.75 g, 5 mmol), followed by refluxing at 55° C. for 24 hours. The solvent was removed in vacuo, and the residue was dissolved by adding ethyl acetate (50 mL) and water (50 mL) thereto. The aqueous layer was separated and the organic layer was washed with saturated brine (30 mL), followed by concentration in vacuo. The residue was purified by column chromatography (hexane:ethyl acetate=4:1) and the solvent was removed in vacuo to give the object compound (13) as a pale yellow viscous liquid (2.76 g, yield 52%).

$^1$H NMR (CDCl$_3$) δ: 1.24 (t, J=7.0Hz, 3H), 1.25 (t, J=7.0Hz, 3H), 1.60-1.90 (m, 2H), 2.47 (t, J=8.1Hz, 2H), 3.73 (s, 3H), 4.24 (q, J=7.0Hz, 2H), 4.26 (q, J=7.0Hz, 2H), 4.25-4.40 (m, 1H), 5.11 (s, 2H), 5.53 (d, J=7.8Hz, 1H), 7.30-7.40 (m, 5H), 7.87 (d, J=8.9Hz, 1H), 8.46 (dd, J=8.9, 2.7Hz, 1H), 9.32 (d, J=2.7Hz, 1H).

EXAMPLE 5

1,6-Dibenzyl (S)-2-tert-butoxycarbonylamino-5-benzyloxycarbonyl-5-(5-nitropyridin-2-yl)hexane dicarboxylate (14) (Method a)

After the compound (5) (4.06 g, 10 mmol) and the compound (3) (3.87 g, 10 mmol) were dissolved in acetone (100 mL) under a nitrogen atmosphere at room temperature, thereto were added potassium carbonate (6.9 g, 50 mmol) and sodium iodide (0.75 g, 5 mmol), followed by refluxing at 55° C. for 24 hours. The solvent was removed in vacuo and the residue was dissolved by adding ethyl acetate (50 mL) and water (50 mL) thereto. The aqueous layer was separated and the organic layer was washed with saturated brine (30 mL), followed by concentration in vacuo. The residue was purified by column chromatography (hexane: ethyl acetate=5:1) and the solvent was removed in vacuo to give the object compound (14) as a pale yellow viscous liquid (3.28 g, yield 47%).

$^1$H NMR (CDCl$_3$) δ: 1.41 (s, 9H), 1.55-1.85 (m, 2H), 2.49 (t, J=8.4Hz, 2H), 4.15-4.25 (m, 1H), 5.05-5.15 (br, 1H), 5.14 (s, 4H), 5.20 (s, 2H), 7.05-7.38 (m, 15H), 7.82 (d, J=8.5Hz, 1H), 8.40 (dd, J=8.5, 2.5Hz, 1H), 9.30 (d, J=2.5Hz, 1H).

EXAMPLE 6

1-Methyl, 6-ethyl (S)-2-tert-butoxycarbonylamino-5-ethyloxycarbonyl-5-(5-nitropyridin-2-yl)hexane dicarboxylate (15) (Method a)

After the compound (9) (2.82 g, 10 mmol) and the compound (4) (3.43 g, 10 mmol) were dissolved in acetone (100 mL) under a nitrogen atmosphere at room temperature, thereto were added potassium carbonate (6.9 g, 50 mmol), followed by refluxing at 55° C. for 24 hours. The solvent was removed in vacuo and the residue was dissolved by adding ethyl acetate (50 mL) and water (50 mL) thereto. After separating off the aqueous layer, the organic layer was washed with saturated brine (30 mL) and concentrated in vacuo. The residue was purified by column chromatography (hexane:ethyl acetate=3:1) and the solvent was removed in vacuo to give the object compound (15) as a pale yellow viscous liquid (3.38 g, yield 68%).

$^1$H NMR (CDCl$_3$) δ: 1.20-1.35 (m, 6H), 1.43 (s, 9H), 1.50-1.80 (m, 2H), 2.47 (t, J=8.4Hz, 2H), 3.72 (s, 3H), 4.15-4.45 (m, 5H), 5.15-5.30 (br, 1H) 7.86 (d, J=8.6Hz, 1H), 8.42 (dd, J=8.6, 2.5Hz, 1H), 9.37 (d, J=2.5Hz, 1H).

EXAMPLE 7

1-Benzyl, 7-ethyl (S)-2-tert-butoxycarbonylamino-6-ethoxycarbonyl-6-phenylheptane dicarboxylate (16) (Method a)

After the compound (5) (4.49 g, 10 mmol) and diethyl phenylmalonate (2.36 g, 10 mmol) were dissolved in acetone (100 mL) under a nitrogen atmosphere at room temperature, thereto were added potassium carbonate (6.9 g, 50 mmol), followed by refluxing at 55° C. for 24 hours. The solvent was removed in vacuo and the residue was dissolved by adding ethyl acetate (50 mL) and water (50 mL) thereto. After separating off the aqueous layer, the organic layer was washed with saturated brine (30 mL) and concentrated in vacuo. The residue was purified by column chromatography (hexane: ethyl acetate=8:1) and the solvent was removed in vacuo to give the object compound (16) as a pale yellow viscous liquid (2.71 g, yield 50%).

$^1$H NMR (CDCl$_3$) δ: 1.15-1.35 (m, 6H), 1.43 (s, 9H), 1.55-1.92 (m, 4H), 2.44 (t, J=8.4Hz, 2H), 4.10-4.35 (m, 5H), 5.05-5.12 (br, 1H), 5.14-5.20 (m, 2H), 7.25-7.45 (m, 10H).

EXAMPLE 8

1-Methyl, 5-ethyl (S)-2-tert-butoxycarbonylamino-4-ethoxycarbonyl-4-phenylcarbonylpentane dicarboxylate (17) (Method b)

Sodium hydride (600 mg, 15 mmol:60%) was added to THF (50 ml) under a nitrogen atmosphere at room temperature, and thereto was gradually dropped the compound (11) (377 mg, 10 mmol) diluted with THF (20 ml). After cessation of evolution of hydrogen, thereto was gradually added benzoyl chloride (1.41 mg, 10 mmol) in DMF (10 ml), followed by stirring for 24 hours at 60° C. The mixture was neutralized under ice cooling with 1N hydrochloric acid, and thereto was added ethyl acetate (150 mL). The aqueous layer was separated and the organic layer was washed with saturated brine (100 mL) and concentrated in vacuo. The residue was purified by column chromatography (hexane:ethyl acetate=8:1), and the solvent was removed in vacuo to give the object compound (17) (326 mg, yield 70%).

$^1$H NMR (CDCl$_3$) δ:1.15-1.30 (m, 6H), 1.41 (s, 9H), 2.51-2.58 (m, 2H), 3.70 (s, 3H), 4.15-4.25 (m, 5H), 5.05-5.15 (br, 1H), 7.30-7.50 (m, 3H), 7.82-7.94 (m, 2H).

EXAMPLE 9

1-Methyl, 6-benzyl (S)-3-tert-butoxycarbonylamino-5-benzyloxycarbonyl-5-(5-nitropyridin-2-yl)hexane dicarboxylate (18) (Method a)

After the compound (7) (3.11 g, 10 mmol) and the compound (8) (4.06 g, 10 mmol) were dissolved in acetone (100 mL) under a nitrogen atmosphere at room temperature, thereto were added potassium carbonate (6.9 g, 50 mmol) and sodium iodide (0.75 g, 5 mmol), followed by refluxing at 55° C. for 24 hours. The solvent was removed in vacuo and the residue was dissolved by adding ethyl acetate (50 mL) and water (50 mL) thereto. After separating off the aqueous layer, the organic layer was washed with saturated brine (30 mL) and concentrated in vacuo. The residue was purified by column chromatography (hexane:ethyl acetate=3:1) and the solvent was removed in vacuo to give the object compound (18) as a pale yellow viscous liquid (2.73 g, yield 44%).

$^1$H NMR (CDCl$_3$) δ: 1.45 (s, 9H), 2.41-2.74 (m, 4H), 3.72 (s, 3H), 3.98-4.09 (m, 1H), 5.00-5.15 (br, 1H), 5.15-5.26 (m, 4H), 7.15-7.35 (m, 10H), 7.80 (d, J=8.5Hz, 1H), 8.41 (dd, J=8.5, 2.5Hz, 1H), 9.32 (d, J=2.5Hz, 1H).

EXAMPLE 10

Methyl (S)-2-tert-butoxycarbonylamino5-(5-aminopyridin-2-yl)pentanoate (19)

To a solution of the compound (12) (3.11 g, 5 mmol) in methanol (30 mL) was added 10% palladium/carbon (300 mg) and the mixture was stirred at room temperature for 24 hours under a hydrogen atmosphere at ordinary pressure. The palladium/carbon was filtered off and the filtrate was concentrated in vacuo. To the residue was toluene (50 mL), followed by stirring at 100° C. for 5 hours (pH=7). After confirming cessation of evolution of carbon dioxide, the organic layer was concentrated in vacuo to give the object compound (19) as a yellow viscous liquid (1.37 g, yield 85%). Optical purity; >99% ee $^1$H NMR (CDCl$_3$) δ: 1.42 (s, 9H), 1.60-1.90 (m, 4H), 2.65-2.78 (m, 2H), 3.57 (s, 2H), 3.71 (s, 3H), 4.25-4.35 (m, 1H), 5.07-5.17 (br, 1H), 6.90-6.92 (m, 2H), 8.02 (d, J=2.5Hz, 1H).

EXAMPLE 11

(S)-2-Benzyloxycarbonylamino-5-(5-nitropyridin-2-yl)pentanoic acid (20)

The compound (13) (2.66 g, 5 mmol) was dissolved in methanol (30 mL) and water (10 mL) under a nitrogen atmosphere at room temperature, and thereto was added lithium hydroxide monohydrate (693 mg, 16.5 mmol) at 0° C. The mixture was stirred at room temperature for 24 hours and carefully neutralized with 1N hydrochloric acid (16.5 mmol) under ice cooling, followed by extraction with ethyl acetate (30 mL). The organic layer was washed with saturated brine (20 mL) and stirred at 40° C. for 30 minutes (pH=4). After confirming cessation of evolution of carbon dioxide, the solvent was removed in vacuo to give the compound (20) as a pale yellow solid (1.49 g, yield 80%). Optical purity: >99% ee $^1$H NMR (CDCl$_3$) δ: 1.70-2.00 (m, 4H), 2.86-3.06 (m, 2H), 4.45 (br, 1H), 5.11 (s, 2H), 5.64 (d, J=7.6Hz, 1H), 7.26-7.40 (m, 6H), 8.43 (dd, J=8.4, 2.4Hz, 1H), 9.39 (d, J=2.4Hz, 1H), 10.00-10.90 (br, 1H).

EXAMPLE 12

(S) -2-tert-Butoxycarbonylamino-5-(5-aminopyridin-2-yl)pentanoic acid (21)

To a solution of the compound (14) (1.39 g (2 mmol) in methanol (15 mL) was added 10% palladium/carbon (150 mg) and the mixture was stirred at room temperature for 24 hours under a hydrogen atmosphere at ordinary pressure. The palladium/carbon was filtered off and the filtrate was concentrated in vacuo. To the residue was toluene (50 mL), followed by stirring at 100° C. for 5 hours (pH=7). After confirming cessation of evolution of carbon dioxide, the organic layer was concentrated in vacuo to give the object compound (21) as a pale yellow viscous liquid (544 mg, yield 88%). Optical purity; >99% ee.

$^1$H NMR (D$_2$O) δ: 1.41 (s, 9H), 1.55-1.85 (m, 4H), 2.83 (t, J=7.0Hz, 2H), 3.75-3.95 (m, 1H), 7.50 (d, J=8.0Hz, 1H), 7.66 (dd, J=8.0, 2.5Hz, 1H), 7.92 (d, J=2.5Hz, 1H).

EXAMPLE 13

(S)-2-tert-Butoxycarbonylamino-5-(5-nitropyridin-2-yl)pentanoic acid (22)

The compound (15) (2.48 g, 5 mmol) was dissolved in methanol (30 mL) and water (10 mL) under a nitrogen atmosphere at room temperature, and thereto was added lithium hydroxide monohydrate (693 mg, 16.5 mmol) at 0° C. The mixture was stirred at room temperature for 24 hours, carefully neutralized with 1N hydrochloric acid (16.5 mmol) under ice cooling, and then extracted with ethyl acetate (30 mL). The organic layer was washed with saturated brine (20 mL) and stirred at 40° C. for 30 minutes (pH=4). After confirming cessation of evolution of carbon dioxide, the solvent was removed in vacuo to give the compound (22) as a pale yellow solid (1.35 g, yield 80%). Optical purity: >99% ee $^1$H NMR (CDCl$_3$) δ:1.45 (s, 9H), 1.70-2.00 (m, 4H), 2.86-3.06 (t, J=7.5, 2H), 4.30-4.40 (m, 1H), 5.23 (d, J=7.6Hz, 1H), 7.40 (d, J=8.0Hz, 1H), 8.43 (dd, J=8.0, 2.4Hz, 1H), 9.40 (d, J=2.4Hz, 1H).

EXAMPLE 14

(S)-2-tert-Butoxycarbonylamino-6-phenylhexanoic acid (23)

The compound (16) (2.71 g, 5 mmol) was dissolved in methanol (30 mL) and water (10 mL) under a nitrogen atmosphere at room temperature, and thereto was added lithium hydroxide monohydrate (693 mg, 16.5 mmol) at 0° C. The mixture was stirred at room temperature for 24 hours, carefully neutralized with 1N hydrochloric acid (16.5 mmol) under ice cooling, and then extracted with ethyl acetate (30 mL). The organic layer was washed with saturated brine (20 mL) and stirred at 80° C. for 5 hours (pH=4). After confirming cessation of evolution of carbon dioxide, the solvent was removed in vacuo to give the compound (23) as a pale yellow solid (1.23 g, yield 80%). Optical purity: >99% ee $^1$H NMR (CDCl$_3$) δ: 1.48 (s, 9H), 1.50-2.10 (m, 6H), 2.56-2.66 (m, 2H), 4.45 (m, 1H), 5.16 (s, 1H), 7.25-7.45 (m, 5H).

EXAMPLE 15

(S)-2-tert-Butoxycarbonylamino-5-oxo-5-phenylpentanoic acid (24)

The compound (17) (2.40 g, 5 mmol) was dissolved in methanol (30 mL) and water (10 mL) under a nitrogen atmosphere at room temperature, and thereto was added lithium hydroxide monohydrate (693 mg, 16.5 mmol) at 0° C. The mixture was stirred at room temperature for 24 hours, carefully neutralized with 1N hydrochloric acid (16.5 mmol) under ice cooling, and then extracted with ethyl acetate (30 mL). The organic layer was washed with saturated brine (20 mL) and stirred at 60° C. for 3 hours (pH=4). After confirming cessation of evolution of carbon dioxide, the solvent was removed in vacuo to give the compound (24) as a pale yellow liquid (1.24 g, yield 77%). Optical purity: >99% ee $^1$H NMR (CDCl$_3$) δ: 1.42 (s, 9H), 1.80-2.10 (m, 2H), 3.33 (t, J=7.4Hz, 2H), 4.09-4.16 (m, 1H), 5.09-5.19 (br, 1H), 7.28-7.44 (m, 3H), 7.82-7.92 (m, 2H).

EXAMPLE 16

Methyl (S)-3-tert-butoxycarbonylamino-5-(5-aminopyridin-2-yl)pentanoate (25)

To a solution of the compound (18) (3.11 g, 5 mmol) in methanol (30 mL) was added 10% palladium/carbon (300 mg) and the mixture was stirred at room temperature for 24 hours under a hydrogen atmosphere at ordinary pressure. The palladium/carbon was filtered off and the filtrate was concentrated in vacuo. To the residue was added toluene (50 mL), followed by stirring at 100° C. for 5 hours (pH=7). After confirming cessation of evolution of carbon dioxide, the organic layer was concentrated in vacuo to give the object compound (25) as a yellow viscous liquid (1.29 g, yield 80%). Optical purity; >99% ee.

$^1$H NMR (CDCl$_3$) δ: 1.42 (s, 9H), 1.80-1.97 (m, 2H), 2.49-2.78 (m, 4H), 3.76 (s, 3H), 4.05-4.15 (m, 1H), 5.07-5.17 (br, 1H), 6.90-6.99 (m, 2H), 8.07 (d, J=2.5Hz, 1H).

INDUSTRIAL APPLICABILITY

The present invention relates to a process for the preparation of a nonnatural amino acid useful as an intermediate of a medicament or an agrochemical.

The invention claimed is:

1. A process for the preparation of a nonnatural amino acid represented by the following formula (C):

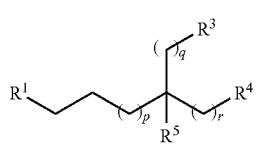

(C)

which is characterized by deprotecting protective groups of carboxyl groups in the malonic acid moiety of the compound represented by following formula (B):

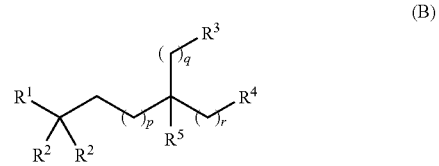

(B)

and then subjecting the resulting compound to elimination of two carbon dioxide molecules (step 2) to prepare said nonnatural amino acid (C), wherein $R^1$ is a substituted or unsubstituted aromatic group, a substituted or unsubstituted and unsaturated heterocyclic group, or $R^6$CO group, $R^2$ and $R^3$ are independently a protected carboxyl group, $R^4$ is a protected amino group, $R^5$ is hydrogen atom, a substituted or unsubstituted and saturated or unsaturated aliphatic hydrocarbon group, a substituted or unsubstituted aromatic group, or a substituted or unsubstituted and saturated or unsaturated heterocyclic group, $R^6$ is a substituted or unsubstituted and saturated or unsaturated aliphatic hydrocarbon group, a substituted or unsubstituted aromatic group, or a substituted or unsubstituted and saturated or unsaturated heterocyclic group, and p, q and r are independently an integer of 0 to 10.

2. A process for the preparation of a nonnatural amino acid represented by the following formula (C):

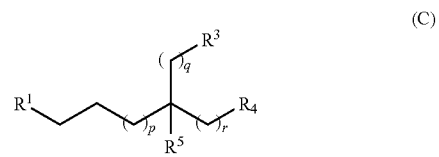

(C)

which is characterized by reacting a terminal constituent compound represented by the following formula (A1), a malonic acid derivative represented by the following formula (A2) and a starting material amino acid represented by the following formula (A3):

(A1)

(A2)

(A3)

to prepare a compound represented by the following formula (B) (step 1):

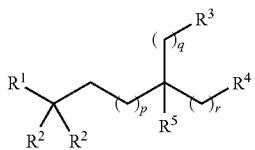

(B)

and then subjecting the compound (B) to deprotection of protective groups of carboxyl groups in $R^2$ and to decarboxylation to prepare said compound (C) (step 2), wherein, $X^1$ and $X^2$ is a leaving group, $R^1$ is a substituted or unsubstituted aromatic group, a substituted or unsubstituted and unsaturated heterocyclic group, or $R^6CO$ group, $R^2$ and $R^3$ are independently a protected carboxyl group, $R^4$ is a protected amino group, $R^5$ is hydrogen atom, a substituted or unsubstituted and saturated or unsaturated aliphatic hydrocarbon group, a substituted or unsubstituted aromatic group, or a substituted or unsubstituted and saturated or unsaturated heterocyclic group, $R^6$ is a substituted or unsubstituted and saturated or unsaturated aliphatic hydrocarbon group, a substituted or unsubstituted aromatic group, or a substituted or unsubstituted and saturated or unsaturated heterocyclic group, and p, q and r are independently an integer of 0 to 10.

3. The process for the preparation of a nonnatural amino acid (C) according to claim 2, wherein the step 1 is carried out in the presence of a base.

4. The process for the preparation of a nonnatural amino acid (C) according to claim 2, wherein in the step 1, after reaction of a terminal constituent compound (A1) with a malonic acid derivative (A2) in the presence of a base, a starting material amino acid (A3) is reacted therewith.

5. The process for the preparation of a nonnatural amino acid (C) according to claim 1 or 2, wherein when the compound (B) in which $R^1$, $R^5$ or $R^6$ is a group substituted by nitro group, is used and subjected to hydrogenolysis in order to deprotect protective groups of carboxyl groups in the step 2, the nitro group is together converted to amino group.

6. The process for the preparation of a nonnatural amino acid (C) according to claim 1 or 2, wherein $R^3$ is alkoxycarbonyl group, $R^4$ is acylamino group, N-phthalimide group, or alkyloxycarbonylamino group, and p, q and r are independently an integer of 0 to 5.

7. The process for the preparation of a nonnatural amino acid (C) according to claim 1 or 2, wherein $R^2$ and $R^3$ are independently alkoxycarbonyl group, $R^4$ is alkyloxycarbonylamino group, $R^5$ is hydrogen atom, and p, q and r are independently an integer of 0 to 3.

8. The process for the preparation of a nonnatural amino acid (C) according to claim 1 or 2, wherein the asymmetric carbon substituted by $R^5$ is optically active.

9. A compound represented by the following formula (B):

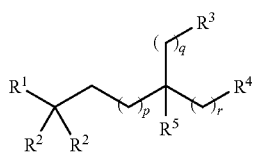

(B)

wherein $R^1$ is a substituted or unsubstituted aromatic group, a substituted or unsubstituted and unsaturated heterocyclic group, or $R^6CO$ group, $R^2$ and $R^3$ are independently a protected carboxyl group, $R^4$ is a protected amino group, $R^5$ is hydrogen atom, a substituted or unsubstituted and saturated or unsaturated aliphatic hydrocarbon group, a substituted or unsubstituted aromatic group, or a substituted or unsubstituted and saturated or unsaturated heterocyclic group, $R^6$ is a substituted or unsubstituted and saturated or unsaturated aliphatic hydrocarbon group, a substituted or unsubstituted aromatic group, or a substituted or unsubstituted and saturated or unsaturated heterocyclic group, and p, q and r are independently an integer of 0 to 10.

10. The compound as claimed in claim 9 wherein $R^3$ is alkoxycarbonyl group, $R^4$ is acylamino group, N-phthalimide group, or alkyloxycarbonylamino group, and p, q and r are independently an integer of 0 to 5.

11. The compound as claimed in claim 9 wherein $R^2$ and $R^3$ are independently alkoxycarbonyl group, $R^4$ is alkyloxycarbonylamino group and p, q and r are independently an integer of 0 to 3.

12. The compound as claimed in claim 9 wherein $R^1$ is a substituted or unsubstituted phenyl group, a substituted or unsubstituted and unsaturated heterocyclic group containing nitrogen atom, or a substituted or unsubstituted benzoyl group, $R^2$ and $R^3$ are independently methoxycarbonyl group, ethoxycarbonyl group, propoxycarbonyl group, isopropoxycarbonyl group, allyloxycarbonyl group, benzyloxycarbonyl group or tert-butoxycarbonyl group, $R^4$ is benzyloxycarbonylamino group, tert-butoxycarbonylamino group or 9-fluorenylmethyloxycarbonylamino group, $R^5$ is hydrogen atom, and p, q and r are independently an integer of 0 to 3.

13. The compound as claimed in claim 9 wherein the asymmetric Carbon substituted by $R^5$ is optically active.

* * * * *